United States Patent
Lee et al.

(10) Patent No.: US 6,730,040 B2
(45) Date of Patent: May 4, 2004

(54) 3-POINT RADIAL ARTERY PRESSURE PULSE WAVE TRANSDUCER USING PNEUMATIC SYSTEM

(75) Inventors: Sun Kyu Lee, Kwangju (KR); Jong Jin Lee, Jollanam-do (KR); Byung Ha Ahan, Kwangju (KR); Pyong Woon Park, Daejeon (KR)

(73) Assignee: Kwangju Institute of Science & Technology, Kwangju (KR)

( * ) Notice: Subject to any disclaimer, the term of this patent is extended or adjusted under 35 U.S.C. 154(b) by 21 days.

(21) Appl. No.: 10/125,964

(22) Filed: Apr. 19, 2002

(65) Prior Publication Data

US 2003/0009105 A1 Jan. 9, 2003

(30) Foreign Application Priority Data

Jul. 3, 2001 (KR) .......................... 2001-39582

(51) Int. Cl.[7] .................................. A61B 5/02
(52) U.S. Cl. ...................... 600/485; 600/500
(58) Field of Search ................ 600/485, 490, 600/500–507, 300, 301

(56) References Cited

U.S. PATENT DOCUMENTS

| | | | | |
|---|---|---|---|---|
| 4,423,738 A | * | 1/1984 | Newgard | 600/485 |
| 5,238,000 A | * | 8/1993 | Niwa | 600/502 |
| 5,396,895 A | * | 3/1995 | Takashima et al. | 600/500 |
| 5,461,922 A | * | 10/1995 | Koen | 73/756 |
| 5,722,414 A | * | 3/1998 | Archibald et al. | 600/485 |

OTHER PUBLICATIONS

Lee, Jong–jin; Jeong, Min–suk; Hwang, Sung–ha; Lee, Jong–Hyun; and Lee, Sun–Kye. *Development of a Radial Artery Pulse Wave Tranducer for Diagnosis of Human Body Constitution*, Proceedings of the 32$^{nd}$ ISR (International Symposiumon Robotics), held in Kwangju, Korea on Apr. 19–21, 2001.

* cited by examiner

*Primary Examiner*—Robert L. Nasser
*Assistant Examiner*—Patricia Mallari
(74) *Attorney, Agent, or Firm*—Jones Day

(57) ABSTRACT

The present invention relates to a pressure pulse wave transducer for sensing change of the blood pressure in vivo and for converting it into an electrical signal to detect the arterial pressure pulse wave.

5 Claims, 6 Drawing Sheets

3-POINT RADIAL ARTERY PRESSURE PULSE WAVE TRANSDUCER USING PNEUMATIC SYSTEM

1. FIELD OF THE INVENTION

The present invention generally relates to a radial artery pressure pulse wave transducer for sensing a change in the pressure of the blood vessels in vivo, and converting the sensed result into an electrical signal to detect a pressure pulse wave. Specifically, the invention relates to a device for equal pressure distribution at given sensing points by using a pneumatic system for improved tightness and simultaneous conversion of force transferred through an air medium into an electrical signal to detect the pressure pulse wave.

2. DESCRIPTION OF THE PRIOR ART

Blood pressure is measured to diagnose human body condition so that a medical practitioner can determine whether or not an individual has a cardiovascular-related disease.

There is a conventional blood pressure measuring system which employs a method by which an electronic sensor such as a piezoelectric device, etc., directly contacts the human body to measure a change in the pressure within the blood vessel. This conventional blood pressure measuring system uses a single measuring point. Recently, several pulse transducers using the three-point measurement system have been developed and utilized in the field of Oriental medicine. However, none of the devices using the three-point measurement system is reliable because there have been mechanical problems due to the non-uniform measuring conditions at the three points.

3. SUMMARY OF THE INVENTION

It is therefore the object of the present invention to provide a pressure pulse wave transducer that assures an accurate 3-point measurement method by using a pneumatic system that applies a uniform pressure at a given sensing point.

To achieve this object, the present invention provides a pressure pulse wave transducer for detecting pulse waves at three points in a person's wrist comprising: a body having a space for longitudinally accepting a wrist; three depressing frames movably installed for contacting the wrist; a pressure means uniformly pressing the depressing frames; three measuring cavities, each installed within the depressing frames and filled with a constant compressed air; contactors which are inserted into the depressing frames and which are attached to the measuring cavities; differential pressure sensors, each connected to ports at one side of the measuring cavities for detecting a pressure change in the measuring cavities; and a reference cavity connected to ports at one side of the differential pressure sensors, said reference cavity having constant pressure, where the contactors apply the same pressure to each of three points, and the pressure sensors measure the pressure difference between the reference cavity and the measuring cavities simultaneously to detect the pulse wave of the radial artery.

4. BRIEF DESCRIPTION OF THE DRAWINGS

The aforementioned aspects and other features of the present invention will be better understood by reading the following detailed description of the embodiments of the invention when considered in conjunction with the accompanying drawings, wherein.

5. DETAILED DESCRIPTION OF THE PREFERRED EMBODIMENTS

The present invention will be described in detail by way of the preferred embodiments with reference to the accompanying drawings.

Figure 1:
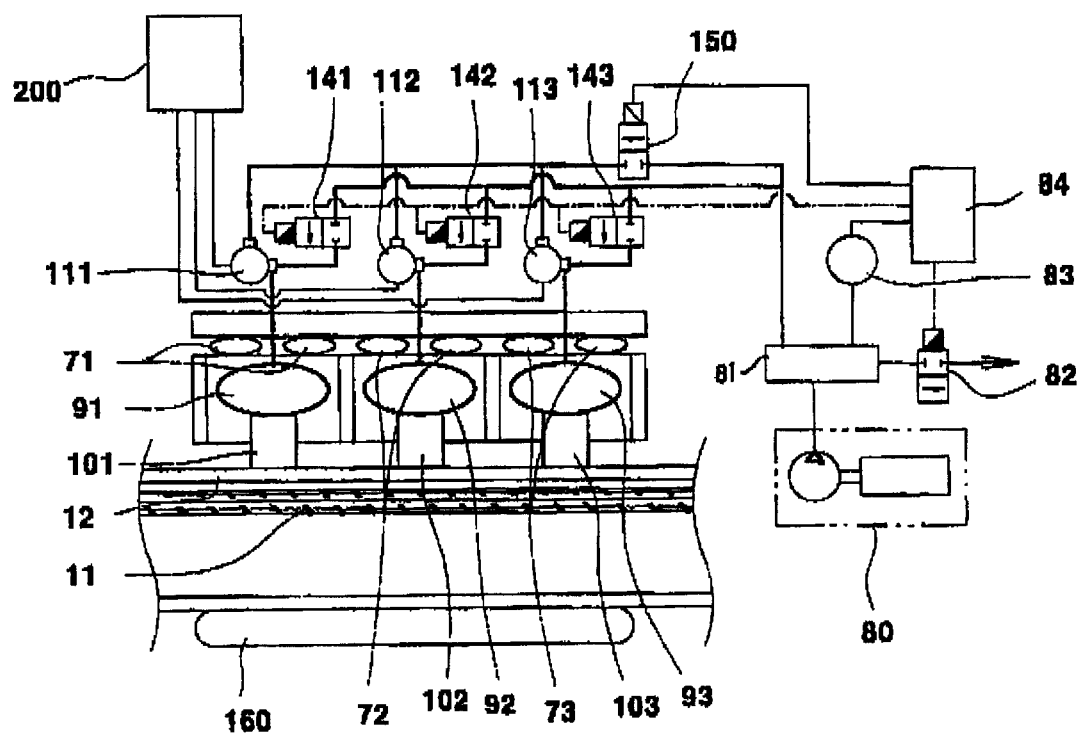
FIG. 1 is a schematic view of the construction of the entire system of a pressure pulse wave transducer.
Figure 2:
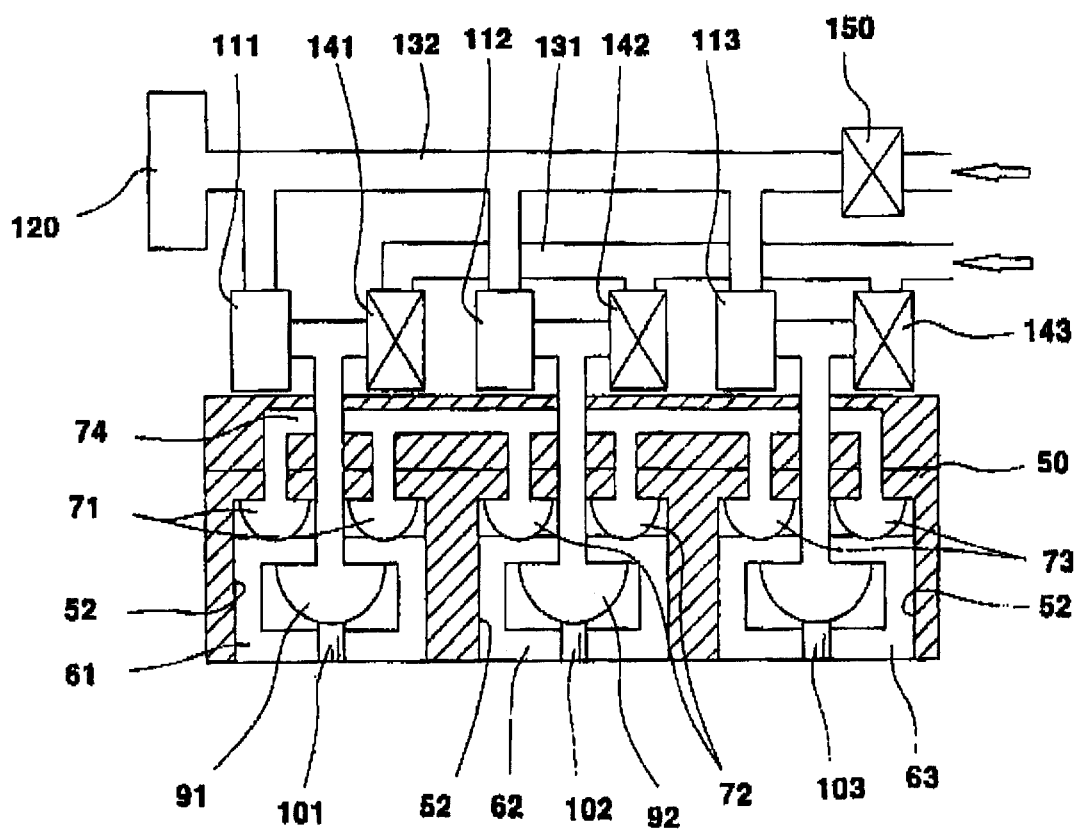
FIG. 2 is a longitudinal cross-sectional view of the pressure pulse wave transducer.

FIG. 1 is a construction of the entire system of a radial artery pressure pulse wave transducer according to the present invention; FIG. 2 is a longitudinal cross-sectional view of the pressure pulse wave transducer according to the present invention; and FIG. 3 is a horizontal cross-sectional view of the radial artery pressure pulse wave transducer.

Figure 3:
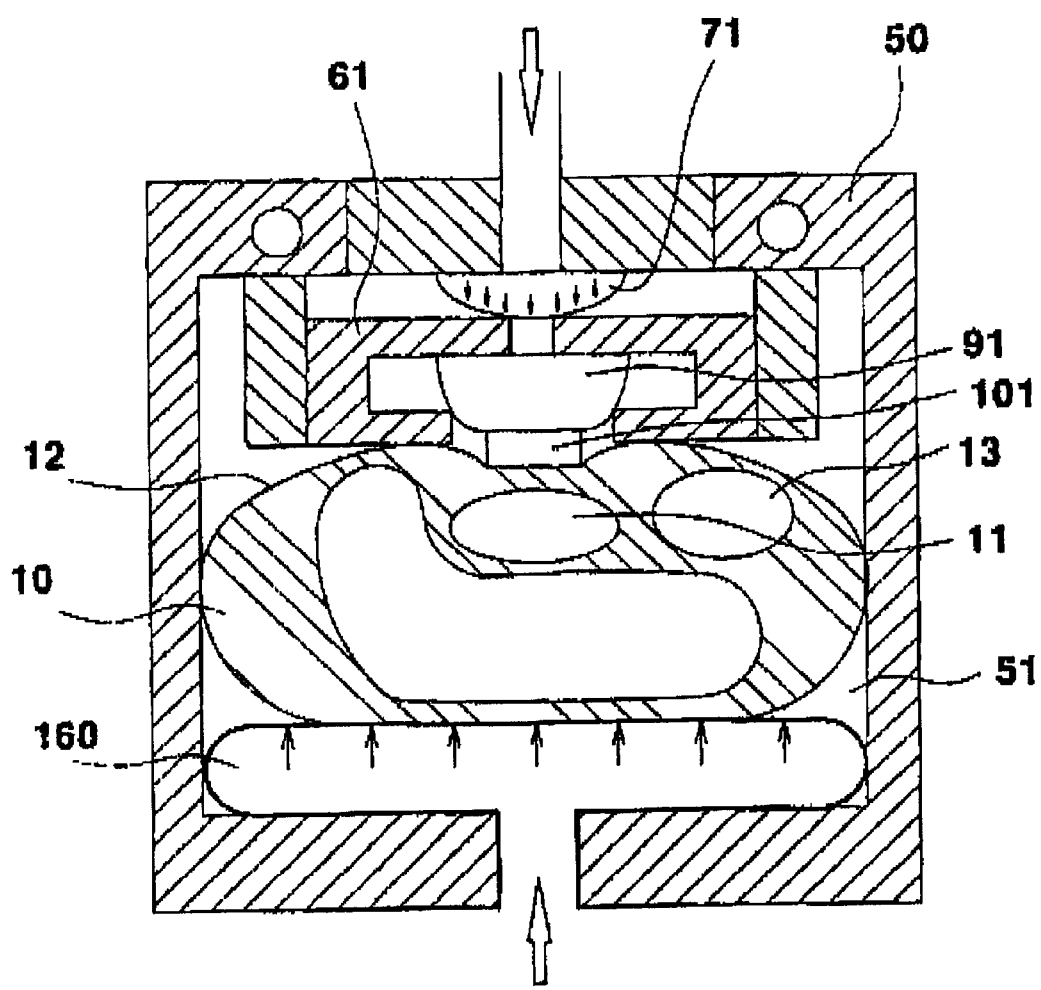
FIG. 3 is a horizontal cross-sectional view of the pressure pulse wave transducer.

As shown in FIGS. 1, 2 and 3, reference numeral 50 indicates a measurement device body. The body 50 has a wrist insertion space 51 into which a wrist 10 is sufficiently inserted in a longitudinal direction, as shown in FIG. 3.

Three depressing frames, 61, 62 and 63, are continuously isolated in a longitudinal direction along the internal top of the body 50. The depressing frames 61, 62 and 63 are installed to move up and down relative to the body 50, and are in contact with the skin 12 of the wrist 10. The depressing frames 61, 62 and 63 press the skin around the radial artery 11 with a uniform and constant pressure at three points based on Pascal's theory.

Figure 4:
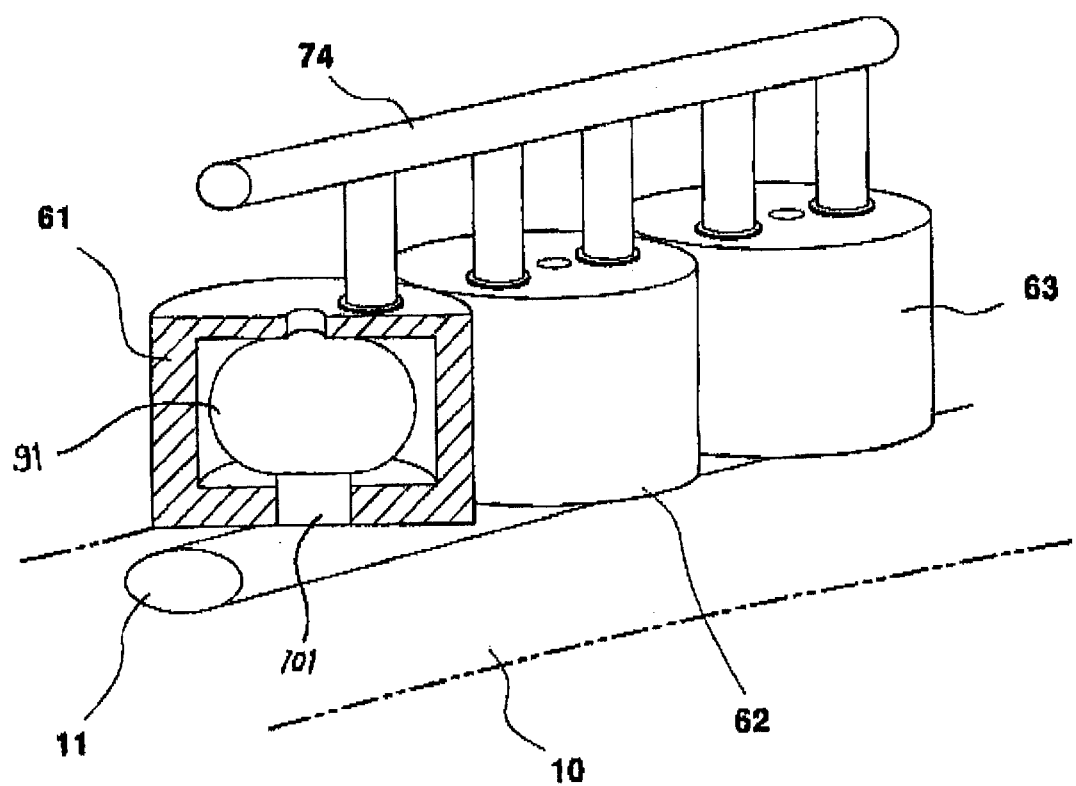
FIG. 4 is a perspective view of a radial artery depressed by the pressure inside the measuring cavity of the pressure pulse wave transducer.

In the present embodiment, the depressing cavities 71, 72 and 73, are each positioned at the upper side of each of the depressing frames 61, 62 and 63 and the lower side of the body 50. The depressing cavities 71, 72 and 73 communicate with each other via a single air supply line 74, as shown in FIGS. 2 and 4. Further, the depressing cavities 71, 72 and 73 have the same pressure set by an air compressor 80 in FIG. 5, which is connected to the air supply line 74. It is preferred that the depressing cavities 71, 72 and 73 are made of a thin material having a resilient property.

The measuring cavities 91, 92 and 93 maintain pressure set by a controller and are isolated from external supplies by closing the solenoid valves 141, 142, and 143 during measurement, and each is installed within the depressing frames 61, 62 and 63, respectively. Contactors 101, 102 and 103 are attached to the bottom of each of the measuring cavities 91, 92 and 93. It is preferred that the measuring cavities 91, 92 and 93 are made of a thin and flexible membrane to satisfy the Principle of Tonometry.

The contactors 101, 102 and 103 are located on the radial artery 11 and serve to transfer the force of the pulse from the radial artery 11 to the measuring cavities 91, 92 and 93.

Therefore, it is preferred that the contactors 101, 102 and 103 are made of a very light material because a quick and high-speed response is required for measurement. Further, the cross sectional area of the contactors 101, 102 and 103 are the same.

The measuring cavities 91, 92 and 93 are connected to ports at one side of differential pressure sensors 111, 112 and 113. These sensors have a high resolution capability, for detecting pressure change within the measuring cavities 91, 92 and 93. Further, a reference cavity 120 is connected to ports at one side of the differential pressure sensors 111, 112 and 113. The reference cavity 120 has the resilient force of a thin film to apply and maintain a constant pressure.

Figure 5:
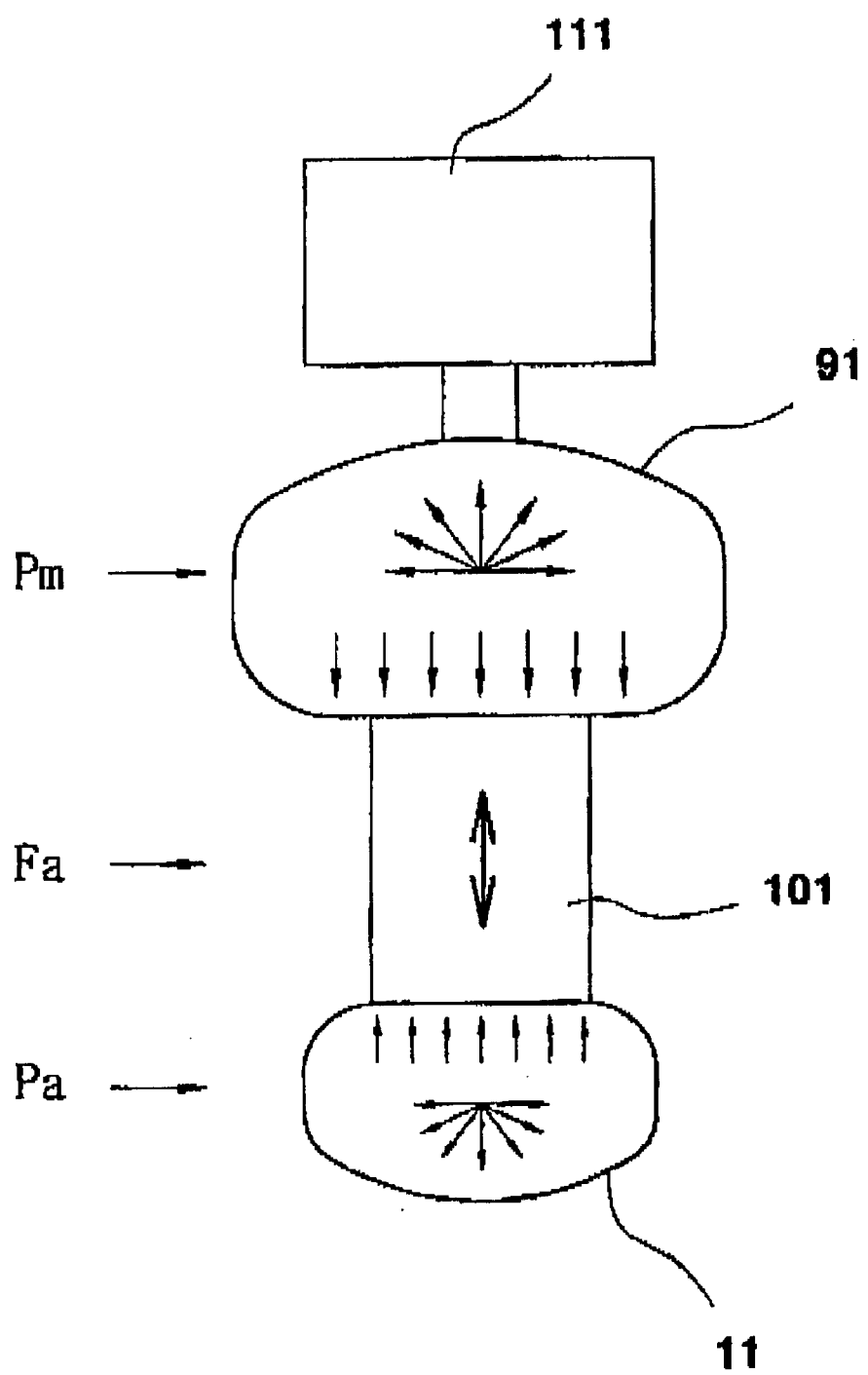
FIG. 5 is a construction of a pressure controller for providing compressed air for the pressure pulse wave transducer.

The air compressor 80 in FIG. 5 supplies compressed air to the measuring cavities 91, 92 and 93 and the reference cavity 120. The air compressor 80 is connected to the measuring cavities 91, 92 and 93 through a first air supply line 131, and to the reference cavity 120 through a second air supply line 132.

Solenoid valves 141, 142 and 143 are installed in the first air supply line 131 in order to open and close the first air supply line 131 to isolate the measuring cavities 91, 92 and 93 from the first air supply line 137 and to maintain the inner pressure of the measuring cavities constant before measurement.

A solenoid 150, for maintaining the pressure exerted by the air compressor 80 between the differential pressure sensors 111, 112 and 113 and the reference cavity 120, is installed in the second air supply line 132, to open and close the second tube.

A wrist depressing tube 160 supports the wrist from the bottom within the body 50, allowing the depressing frames 61, 62 and 63 to be supported steadily against the tendon 13 of the wrist and the radius bone (not shown), thus allowing the contactors 101, 102 and 103 to easily contact the radial artery 11. The wrist depressing tube 160 is connected to the air compressor 80 and is thus filled with compressed air at a set pressure by means of a controller 84. In other words, a solenoid valve (not shown) is installed at the side of the wrist depressing tube 160 and can be opened and closed by a command from the controller 84.

FIG. 5 shows a condition wherein the air compressor 80 is controlled by a known PWM (pulse width modulation) control method, wherein the pressure within a compressed air storage 81 at the air compressor 80 is transmitted to the controller 84 by means of a gauge pressure sensor 83, and the opening and closing of the solenoid valve 82 is thus controlled to generate a continuous pressure. In other words, the air compressed in the air compressor 80 is stored at the air storage 81 and the amount of air exhausted is then controlled by the duty ratio of a square wave to adjust the opening/closing time of the solenoid valve 82 connected to the air storage 81.

An operation of the pressure generator is described below.

As shown in FIG. 3, the wrist 10 is located in the wrist insertion space 51 of the measurement device body 50. If the air compressor 80 of FIG. 5 is then driven, the air storage 81 is filled with a compressed air. Then, the compressed air is supplied to the measuring cavities 91, 92 and 93 via the solenoid valves 141, 142 and 143 that are open and connected to the first air supply line 131. At the same time, the compressed air is supplied to the reference cavity 120 via the solenoid valve 150 that is open and connected to the second air supply line 132.

At this time, the pressure signal sensed by the gauge pressure sensor 83 in FIG. 5 is applied to the controller 84. The solenoid valves 141, 142, 143 and 150 are opened by means of the controller 84 until the respective containers each reach their respective set pressures.

At the same time, compressed air is also supplied to depressing cavities 71, 72 and 73 for equal pressure distribution and the wrist depressing tube 160 by the air compressor 80.

As such, if the compressed air in the measuring cavities 91, 92 and 93, the reference cavity 120, the depressing cavities 71, 72 and 73, and the wrist depressing tube 160, each reach the pressure set in the controller 84, the solenoids 141, 142, 143 and 150 respectively connected to the containers are closed.

Therefore, the pressure on one side of the reference cavity 120 that communicates with the ports at one side of the differential pressure sensors 111, 112 and 113, and the pressure on the side of the measuring cavities 91, 92 and 93 are the same. Thus, there is no difference between the pressure in the differential pressure sensors 111, 112 and 113 and the pressure on the side of the measuring cavities 91, 92 and 93.

Meanwhile, the pressure formed in the depressing cavities 71, 72 and 73 serves to constantly press the depressing frames 61, 62 and 63 downwardly with a constant force. At the same time, the pneumatics applied to the wrist depressing tube 160 supports the wrist from the bottom.

Thus, the depressing frames 61, 62 and 63 apply a uniform force along the radial artery 11. At the same time, the contactors 101, 102 and 103 each attached to the measuring cavities 91, 92 and 93, are protruded by some degree from the lower center of the depressing frames 61, 62 and 62, so that they press the radial artery 11 with a given pressure. At this time, the differential pressure sensors 111, 112 and 113 measure the difference in the pressure that is generated between the reference cavity 120 and the measuring cavities 91, 92 and 93 at each of three points along the radial artery 11. The measured difference in the pressure is transferred to the display and data storage unit 200, which then displays it as a waveform. In other words, according to the present invention, the force of the pulse of the radial artery 11 is transferred to the measuring cavities 91, 92 and 93 via respective contactors 101, 102 and 103 located at the three points. The pressure change in the measuring cavities 91, 92 and 93 is detected and compared with the pressure inside the reference cavity by the differential pressure sensors 111, 112 and 113.

Therefore, as can be understood by reference to FIG. 5, assuming that the area of each contactor 101, 102 and 103 is "A", the pressure within the radial artery 11 is "Pa", the resultant force transferred to each of the contactors 101, 102 and 103 by means of the force exerted by pressure change inside the radial artery 11 is "Fa", the pressure generated within the measuring cavities for measurement 91, 92 and 93 by means of the transfer force Fa is "Pm", and the longitudinal cross section of the contactors is "A", thus, $$Fa = Pa \times A$$

$$Pm = Fa/A,$$

As a result, Pa=Pm.

In other words, the present invention uses a method by which the pressure Pm is obtained by using contactors 101, 102 and 103 and maintaining a constant contact area with both measuring cavity and radial artery based on the Principle of Tonometry.

Figure 6A:
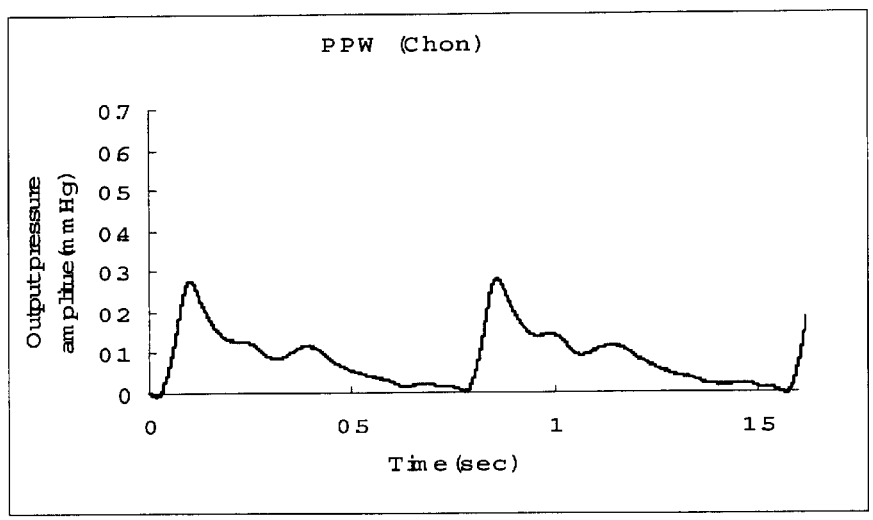
FIGS. 6A, 6B, and 6C are the graphs of pressure as a function of time as measured by a pulse measurement device of the present invention.
Figure 6B:
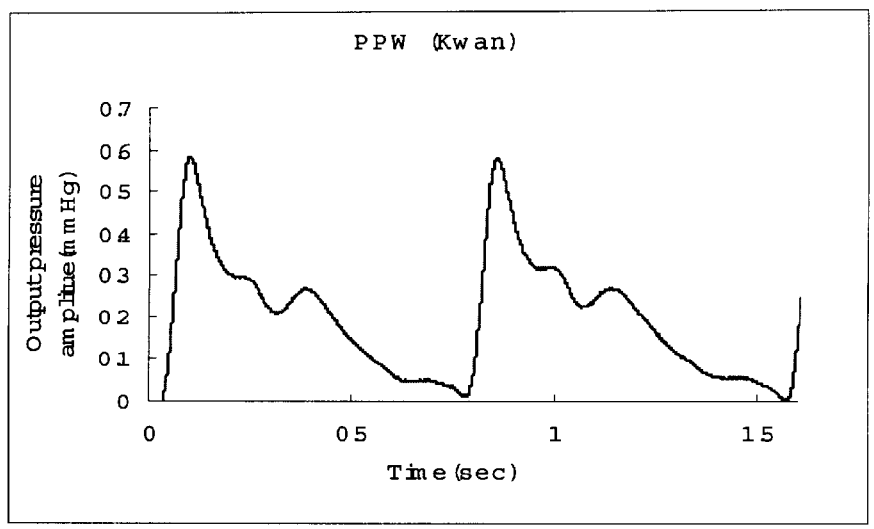
Figure 6C:
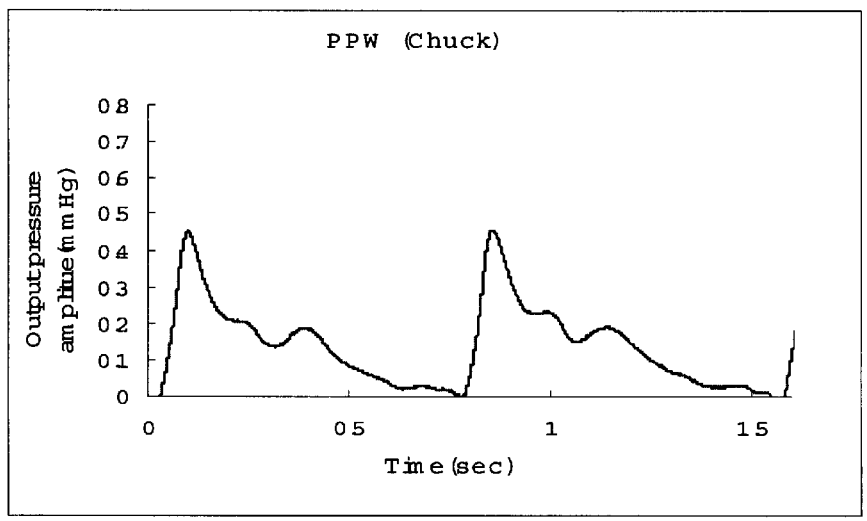

As such, examples of graphs that are displayed through a pulse measurement device of the present invention are shown in FIGS. 6A, 6B and 6C.

As mentioned above, according to the present invention, the pulse pressure of the radial artery at three points differs from the pressure within the measuring cavity for measurement via the contactors, which is then measured by means of the differential pressure sensors. Therefore, the present invention has an outstanding advantage over the prior art in that it can increase the resolution of the signal by comparing pressure inside the measuring cavity with the constant pressure maintained in the reference cavity.

Further, the present invention will improve the tightness of a conventional three-point measurement device in which the wrist directly contacts the piezoelectric device in order to measure the blood pressure.

The present invention has been described with reference to a particular embodiment in connection with a particular application. Those having ordinary skill in the art and access to the teachings of the present invention will recognize additional modifications and applications within the scope thereof. It is therefore intended by the appended claims to cover any and all such applications, modifications, and embodiments within the scope of the present invention.

What is claimed is:

1. A pressure pulse wave transducer for detecting pulse waves at three points of the human's wrist, comprising:

a body having a space for longitudinally accepting a wrist;

three depressing frames for contacting the wrist;

a pressure means for uniformly pressing the depressing frames;

three measuring cavities, each installed within the depressing frames and filled with a constant compressed air;

contactors located in the depressing frames and are attached to the measuring cavities;

differential pressure sensors, each connected to ports at one side of the measuring cavities for detecting pressure changes in the measuring cavities; and a reference cavity connected to ports at one side of the differential pressure sensors, said reference cavity having constant pressure, where the contactors apply the same pressure to each of three points, and the pressure sensors simultaneously measure the pressure differences between the reference cavity and the measuring cavities to detect the pulse wave of a radial artery.

2. The pressure pulse wave transducer of claim 1, wherein said pressure means includes depressing cavities for equal pressure distribution that communicate with each other and are positioned at an upper side of the depressing frames and wherein said depressing cavities for equal pressure distribution have preset pneumatics.

3. The pressure pulse wave transducer of claim 1, wherein the measuring cavities and the reference cavity are connected to an air compressor using first and second air supply lines; said pressure pulse wave transducer further including solenoid valves for isolating the measuring cavities from the first air supply line, whereby compressed air is supplied by the air compressor; and said air compressor including a controller for controlling a consecutive generation of a pressure, which is connected to a gauge pressure sensor for measuring the pressure in the air compressor.

4. The pressure pulse wave transducer of claim 1, wherein said differential pressure sensors are connected to a display and data storage unit for storing measured data and then displaying data in a wave form.

5. The pressure pulse wave transducer of claim 1, further including a wrist depressing tube built into an internal lower side of the body for pressing the wrist upwardly, wherein said wrist depressing tube is connected to an air compressor and is constructed to form a set pressure by means of a controller.

* * * * *